(12) United States Patent
Alexeeva et al.

(10) Patent No.: US 8,178,324 B2
(45) Date of Patent: May 15, 2012

(54) DERACEMISATION OF AMINES

(75) Inventors: Marina Victorovna Alexeeva, Edinburgh (GB); Alexis Enright, Glasgow (GB); Mahmoud Mahmoudian, London (GB); Nicholas Turner, Edinburgh (GB)

(73) Assignee: Ingenza Limited, Midlothian (GB)

( * ) Notice: Subject to any disclaimer, the term of this patent is extended or adjusted under 35 U.S.C. 154(b) by 0 days.

(21) Appl. No.: 12/947,164

(22) Filed: Nov. 16, 2010

(65) Prior Publication Data

US 2011/0065154 A1 Mar. 17, 2011

Related U.S. Application Data

(60) Continuation of application No. 11/685,939, filed on Mar. 14, 2007, now abandoned, which is a division of application No. 10/508,356, filed as application No. PCT/GB03/01198 on Mar. 19, 2003, now Pat. No. 7,208,302.

(30) Foreign Application Priority Data

Mar. 19, 2002 (GB) ................................. 0206415.2

(51) Int. Cl.
*C12P 21/06* (2006.01)
*C12P 13/00* (2006.01)
*C12N 9/06* (2006.01)

(52) U.S. Cl. .......................... 435/128; 435/106; 435/191

(58) Field of Classification Search .................... None
See application file for complete search history.

(56) References Cited

U.S. PATENT DOCUMENTS

| | | | |
|---|---|---|---|
| 6,365,380 B2 | 4/2002 | Liu et al. | |
| 2003/0056245 A1* | 3/2003 | Chatterjee et al. | 800/279 |

OTHER PUBLICATIONS

Chica et al. Curr Opin Biotechnol. Aug. 2005; 16(4):378-84.*
F.R. Alexandre et. al., Amine-boranes : effective reducing agents for the deracemisation of dl-amino acids using l-amino acid oxidase from Proteus myxofaciens, *Tetrahedron Lett.* (2002) 43, 707-710.
M. Alexeeva et. al., Deracemization of alpha-methylbenzylamine using an enzyme obtained by in vitro evolution, *Angewandte Chemie* (2002) 41, 3177-3180.
F.H. Arnold, Design by Directed Evolution, *Acc. Chem. Res.* (1998) 31, 125.
F. Balkenhohl et. al., Optically Active Amines via Lipase-Catalyzed Methoxyacetylation, *J. Prak Chem.* (1997) 339, 381.
T. Beard et. al., Deracemisation and stereoinversion of alpha-amino acids using D-amino acid oxidase and hydride reducing agents, *Chem. Commun.* (2002) 246-247.
R. Bockholt et. al., Partial amino acid sequence of an L-amino acid oxidase from the cyanobacterium Synechococcus PCC6301, cloning and DNA sequence analysis of the aoxA gene, *Biochim. Biophys. Acta* (1995) 289.

P.L. Dostert et. al.,Interactions of Monoamine Oxidase with Substrates and Inhibitors, *Medicinal Research Reviews* (1989) 9, 45-89.
A. Enright et. al., Stereoinversion of β- and γ-substituted α-amino acids using a chemo-enzymatic oxidation reduction procedure, *Chem. Comm.* (2003) 2636-2637.
R. M. Geha et. al., Substrate and inhibitor specificities for human monoamine oxidase A and B are influenced by a single amino acid, *J. Biol. Chem.* (2001) 276, 9877-9882.
E.W. Hafner & D. Wellner, Demonstratio of Imino Acids as Products of the Reactions Catalyzed by D- and L-Amino Acid Oxidases, *Proc. Natl. Acad. Sci.* (1971) 68, 987-991.
G. Heiber & K. Ditrich, Introducing ChiPros™—Biocatalytic production of chiral intermediates on a commercial scale, *Chimica Oggi* (2001) 19, 16-20.
J.W. Huh et. al., Synthesis of L-Proline from the Racemate by Coupling of Enzymatic Enantiospecific Oxidation and Chemical Non-Enantiospecific Reduction, *J. Ferment Bioeng.* (1992) 74, 189.
J.W. Huh et. al., Total Conversion of Racemic Pipecolic Acid into the L-entantiomer by Combination of enantiospecific Oxidation with D-Amino Acid Oxidase and Reduction with Sodium Borohydride, *Biosci. Biotech. Biochem* .(1992) 56, 2081-2.
L.E. Iglesias et. al., Candida antarctica B lipase catalysed resolution of (±)-1-(heteroaryl)ethylamines, *Tetrahedron: Asymmetry* (1997) 8, 2675-2677.
W. Kroutil et. al., Deracemization of compounds possessing a sec-alcohol or -amino group through a cyclic oxidation-reduction sequence : a kinetic treatment *Tetrahedron: Asymmetry* (1998) 9, 2901-2913.
G. Matcham et. al., Enzyme and Reaction Engineering in Bio-catalysis: Synthesis of (S)-methoxyisopropyl-amine (= (S)-1-Methoxypropan-2-amine) *Chimia* (1999) 53, 584-589.
N. Ohrner et. al., Kinetic resolutions of amine and thiol analogues of secondary alcohols catalyzed by teh *Candida Antarctica* lipase B, *Enzyme Microb. Tech.* (1996) 19, 328-331.
M.T. Reetz & K. Schimossek, Lipase-Catalyzed Dynamic Kinetic Resolution of Chiral Amines: Use of Palladium as the Racemization Catalyst, *Chimia* (1996) 50, 668-669.
M.T. Reetz et. al., A Method for High-Throughput Screening of Enantioselective Catalysts, *Angew. Chem. Int. Ed. Engl.* (1999) 38, 1758.
S.O. Sablin et. al., Isolation and characterization of an evolutionary precursor of human monoamine oxidases A and B, *Eur. J. Biochem.* (1998) 253, 270.
B. Schilling & K. Lerch, Amine Oxidases from Aspergillus Niger: Identification of a Novel Flavin-Dependent Enzyme, *Biochim. Biophys. Acta.* (1995) 1243, 529.

(Continued)

*Primary Examiner* — Tekchand Saidha
*Assistant Examiner* — Md. Younus Meah
(74) *Attorney, Agent, or Firm* — McDermott Will & Emery LLP; Avani C. Macaluso

(57) ABSTRACT

The present invention relates to a method for the deracemization or chiral inversion of chiral amines by enzymatic treatment. The method employs a stereoselective enzymatic conversion and either a non-selective or partially selective chemical or enzymatic conversion, simultaneously or sequentially. The invention also provides a method for selecting a suitable enzyme, particularly a suitable amine oxidase, and for the generation of novel enzymes suitable for use in the deracemization method.

6 Claims, 5 Drawing Sheets

OTHER PUBLICATIONS

B. Schilling & K. Lerch, Cloning, Sequencing and Heterologous Expression of the Monoamine Oxidase Gene from *Aspergillus niger*, *Mol. Gen. Genet.* (1995) 247, 430.

J.S. Shin & B.G. Kim, Asymmetric Synthesis of Chiral Amines with ω-Transaminase, *Biotechnology. Bioengineering.* (1999) 65, 206-211.

J.S. Shin et. al., Kinetic Resolution of Chiral Amines with ω-Transaminase Using an Enzyme-Membrane Reactor, *Biotechnology. Bioengineering.* (2001) 73, 179-187.

R.B. Silverman et. al., Stereoselective Ring Opening of 1-Phenylcyclopropylamine Catalyzed by Monoamine Oxidase-B, *J. Am. Chem. Soc.* (1993) 115, 4955.

J.D. Sutherland, Evolutionary optimization of enzymes, *Curr. Opinion. Chem. Biol.* (2000) 263.

Y. Tsugeno et. al., A key amino acid responsible for substate selectivity of monoamine oxidase A and B, *J. Biol. Chem.* (1997) 272, 14033-14036.

N.J. Turner, Functional Group Transformations mediated by Whole Cells and Strategies for the Efficient Synthesis of Optically Pure Chiral Intermediates, *Enzymes in Action*, NATO ASI (ed. B. Zwanenburg) (2000) 71-94.

Chica et al., Curr. Opin. Biotechnol. Aug. 2005: 16(4):378-384.

Bornscheuer et al., Improved biocatalysts by directed evolution and rational protein design, Current Opinion in Chemical Biology, Current Biology Ltd., 5:2, pp. 137-143 (Apr. 1, 2001).

Bornscheuer et al., Directed Evolution of an esterase: screening of enzyme libraries based on ph-indicators and a growth assay, Bioorganic & Medicinal Chemistry, Elsevier Science Ltd, GB, 7:10, pp. 2169-2173 (Oct. 1, 1999).

Liebeton et al., Directed Evolution of an enantioselective lipase, Chemistry and Biology, Current Biology, 7:1, pp. 709718 (Jan. 1, 2000).

Petrounia et al., Designed evolution of enzymatic properties, Current Opinion in Biotechnology, 11:4, pp. 325-330 (Aug. 1, 2000).

Schilling et al., Cloning, sequencing and heterologous expression of the monoamine oxidase gene from *Aspergillus niger*, Mol. Gen. Genet. 247:430-438 (1995).

\* cited by examiner

| Clone | L-AMBA | D-AMBA | L/D |
|---|---|---|---|
| 1 | 0.4 | 0.26 | 1.53 |
| 2 | 1.1 | 0.26 | 4.2 |
| 3 | 0.53 | 0.3 | 1.72 |
| 4 | 1.4 | 0.33 | 4.4 |
| 5 | 0.65 | 0.3 | 2.12 |
| 6 | 0.86 | 0.28 | 3.03 |
| 7 | 1 | 0.28 | 3.7 |
| 8 | 0.73 | 0.28 | 2.6 |
| 9 | 0.35 | 0.18 | 1.8 |
| 10 | 1.2 | 0.3 | 3.9 |
| 11 | 0.57 | 0.32 | 1.8 |
| 12 | 0.53 | 0.22 | 2.4 |
| 13 | 0.43 | 0.296 | 1.45 |
| 14 | 0.74 | 0.3 | 2.45 |
| 15 | 0.44 | 0.26 | 1.65 |
| 16 | 0.715 | 0.29 | 2.4 |
| 17 | 0.35 | 0.26 | 1.33 |
| 18 | 6.6 | 0.21 | 30 |
| 19 | 6.9 | 0.26 | 26 |
| 20 | 0.4 | 0.219 | 1.9 |
| 21 | 0.075 | 0.055 | 1.36 |
| 22 | 0.9 | 0.17 | 4.9 |
| 23 | 0.34 | 0.175 | 1.9 |
| 24 | 1.3 | 0.16 | 8.2 |
| 25 | 0.6 | 0.18 | 3.3 |
| 26 | 0.8 | 0.28 | 2.83 |
| 27 | 0.8 | 0.28 | 2.83 |

FIG. 3

SEQUENCE LISTING

```
<160> NUMBER OF SEQ ID NOS: 9

<210> SEQ ID NO 1
<211> LENGTH: 495
<212> TYPE: PRT
<213> ORGANISM: Aspergillus niger

<400> SEQUENCE: 1

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60
```

```
Thr Leu Leu Leu Glu Ala Arg Asp Arg Ile Gly Gly Arg Ser Trp Ser
 65                  70                  75                  80

Ser Asn Ile Asp Gly Tyr Pro Tyr Glu Met Gly Gly Thr Trp Val His
                 85                  90                  95

Trp His Gln Ser His Val Trp Arg Glu Ile Thr Arg Tyr Lys Met His
            100                 105                 110

Asn Ala Leu Ser Pro Ser Phe Asn Phe Ser Arg Gly Val Asn His Phe
        115                 120                 125

Gln Leu Arg Thr Asn Pro Thr Thr Ser Thr Tyr Met Thr His Glu Ala
    130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
            180                 185                 190

Asp Gln Ile Arg Asp Glu Leu Ser Leu Asn Glu Arg Ser Ser Leu Glu
        195                 200                 205

Ala Phe Ile Leu Leu Cys Ser Gly Gly Thr Leu Glu Asn Ser Ser Phe
    210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
                245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Gly Arg Asp Ala
        275                 280                 285

Ala Arg Val Thr Ala Arg Asp Gly Arg Glu Phe Val Ala Lys Arg Val
    290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Asn
                325                 330                 335

Met Cys Thr Lys Val His Ala Glu Val Asp Asn Met Asp Met Arg Ser
            340                 345                 350

Trp Thr Gly Ile Ala Tyr Pro Phe Asn Lys Leu Cys Tyr Ala Ile Gly
        355                 360                 365

Asp Gly Thr Thr Pro Ala Gly Asn Thr His Leu Val Cys Phe Gly Thr
    370                 375                 380

Asp Ala Asn His Ile Gln Pro Glu Asp Val Arg Glu Thr Leu Lys
385                 390                 395                 400

Ala Val Gly Gln Leu Ala Pro Gly Thr Phe Gly Val Lys Arg Leu Val
                405                 410                 415

Phe His Asn Trp Val Lys Asp Glu Phe Ala Lys Gly Ala Trp Phe Phe
            420                 425                 430

Ser Arg Pro Gly Met Val Ser Glu Cys Leu Gln Gly Leu Arg Glu Lys
        435                 440                 445

His Gly Gly Val Val Phe Ala Asn Ser Asp Trp Ala Leu Gly Trp Arg
    450                 455                 460

Ser Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
```

```
                    485              490              495

<210> SEQ ID NO 2
<211> LENGTH: 495
<212> TYPE: PRT
<213> ORGANISM: Artificial sequence
<220> FEATURE:
<223> OTHER INFORMATION: Variant monoamine oxidase enzyme generated by
      direct evolution

<400> SEQUENCE: 2

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Thr Asn Ile Glu
            20                  25                  30

Asp Thr Asp Lys Asp Gly Pro Trp Asp Val Ile Val Ile Gly Gly Gly
        35                  40                  45

Tyr Cys Gly Leu Thr Ala Thr Arg Asp Leu Thr Val Ala Gly Phe Lys
    50                  55                  60

Thr Leu Leu Leu Glu Ala Arg Asp Arg Ile Gly Gly Arg Ser Trp Ser
65              70                  75                  80

Ser Asn Ile Asp Gly Tyr Pro Tyr Glu Met Gly Gly Thr Trp Val His
            85                  90                  95

Trp His Gln Ser His Val Trp Arg Glu Ile Thr Arg Tyr Lys Met His
        100                 105                 110

Asn Ala Leu Ser Pro Ser Phe Asn Phe Ser Arg Gly Val Asn His Phe
    115                 120                 125

Gln Leu Arg Thr Asn Pro Thr Thr Ser Thr Tyr Met Thr His Glu Ala
130             135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
            165                 170                 175

Val Pro Glu Phe Arg Lys Tyr Asp Glu Met Ser Tyr Ser Glu Arg Ile
        180                 185                 190

Asp Gln Ile Arg Asp Glu Leu Ser Leu Asn Glu Arg Ser Ser Leu Glu
    195                 200                 205

Ala Phe Ile Leu Leu Cys Ser Gly Gly Thr Leu Glu Asn Ser Ser Phe
210                 215                 220

Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
            245                 250                 255

Phe Ala Arg Arg Phe Trp Glu Glu Ala Ala Gly Thr Gly Arg Leu Gly
        260                 265                 270

Tyr Val Phe Gly Cys Pro Val Arg Ser Val Val Asn Glu Arg Asp Ala
    275                 280                 285

Ala Arg Val Thr Ala Arg Asp Gly Arg Glu Phe Val Ala Lys Arg Val
290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Ser
            325                 330                 335

Met Cys Thr Lys Val His Ala Glu Val Asp Asn Met Asp Met Arg Ser
        340                 345                 350

Trp Thr Gly Ile Ala Tyr Pro Phe Asn Lys Leu Cys Tyr Ala Ile Gly
```

```
                   355                 360                 365
Asp Gly Thr Thr Pro Ala Gly Asn Thr His Leu Val Cys Phe Gly Thr
370                 375                 380

Asp Ala Asn His Ile Gln Pro Asp Glu Asp Val Arg Glu Thr Leu Lys
385                 390                 395                 400

Ala Val Gly Gln Leu Ala Pro Gly Thr Phe Gly Val Lys Arg Leu Val
                405                 410                 415

Phe His Asn Trp Val Lys Asp Glu Phe Ala Lys Gly Ala Trp Phe Phe
                420                 425                 430

Ser Arg Pro Gly Met Val Ser Glu Cys Leu Gln Gly Leu Arg Glu Lys
                435                 440                 445

His Gly Gly Val Val Phe Ala Asn Ser Asp Trp Ala Leu Gly Trp Arg
                450                 455                 460

Ser Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
                485                 490                 495

<210> SEQ ID NO 3
<211> LENGTH: 495
<212> TYPE: PRT
<213> ORGANISM: Artificial sequence
<220> FEATURE:
<223> OTHER INFORMATION: Variant monoamine oxidase enzyme generated by
      site directed mutagenesis of the N336S mutant enzyme of SEQ ID
      NO: 2

<400> SEQUENCE: 3

Met Thr Ser Arg Asp Gly Tyr Gln Trp Thr Pro Glu Thr Gly Leu Thr
1               5                   10                  15

Gln Gly Val Pro Ser Leu Gly Val Ile Ser Pro Pro Thr Asn Ile Glu
                20                  25                  30

Asp Thr Asp Lys Asp Gly Pro Trp Asp Val Ile Val Ile Gly Gly Gly
                35                  40                  45

Tyr Cys Gly Leu Thr Ala Thr Arg Asp Leu Thr Val Ala Gly Phe Lys
            50                  55                  60

Thr Leu Leu Leu Glu Ala Arg Asp Arg Ile Gly Gly Arg Ser Trp Ser
65                  70                  75                  80

Ser Asn Ile Asp Gly Tyr Pro Tyr Glu Met Gly Gly Thr Trp Val His
                85                  90                  95

Trp His Gln Ser His Val Trp Arg Glu Ile Thr Arg Tyr Lys Met His
                100                 105                 110

Asn Ala Leu Ser Pro Ser Phe Asn Phe Ser Arg Gly Val Asn His Phe
            115                 120                 125

Gln Leu Arg Thr Asn Pro Thr Thr Ser Thr Tyr Met Thr His Glu Ala
130                 135                 140

Glu Asp Glu Leu Leu Arg Ser Ala Leu His Lys Phe Thr Asn Val Asp
145                 150                 155                 160

Gly Thr Asn Gly Arg Thr Val Leu Pro Phe Pro His Asp Met Phe Tyr
                165                 170                 175

Val Pro Glu Phe Arg Lys Tyr Asp Glu Met Ser Tyr Ser Glu Arg Ile
                180                 185                 190

Asp Gln Ile Arg Asp Glu Leu Ser Leu Asn Glu Arg Ser Ser Leu Glu
            195                 200                 205

Ala Phe Ile Leu Leu Cys Ser Gly Gly Thr Leu Glu Asn Ser Ser Phe
210                 215                 220
```

```
Gly Glu Phe Leu His Trp Trp Ala Met Ser Gly Tyr Thr Tyr Gln Gly
225                 230                 235                 240

Cys Met Asp Cys Leu Ile Ser Tyr Lys Phe Lys Asp Gly Gln Ser Ala
            245                 250                 255

Phe Ala Arg Arg Phe Trp Glu Glu Ala Ala Gly Thr Gly Arg Leu Gly
            260                 265                 270

Tyr Val Phe Gly Cys Pro Val Arg Ser Val Val Asn Glu Arg Asp Ala
            275                 280                 285

Ala Arg Val Thr Ala Arg Asp Gly Arg Glu Phe Val Ala Lys Arg Val
290                 295                 300

Val Cys Thr Ile Pro Leu Asn Val Leu Ser Thr Ile Gln Phe Ser Pro
305                 310                 315                 320

Ala Leu Ser Thr Glu Arg Ile Ser Ala Met Gln Ala Gly His Val Ser
            325                 330                 335

Met Cys Thr Lys Val His Ala Glu Val Asp Asn Lys Asp Met Arg Ser
            340                 345                 350

Trp Thr Gly Ile Ala Tyr Pro Phe Asn Lys Leu Cys Tyr Ala Ile Gly
            355                 360                 365

Asp Gly Thr Thr Pro Ala Gly Asn Thr His Leu Val Cys Phe Gly Thr
            370                 375                 380

Asp Ala Asn His Ile Gln Pro Asp Glu Asp Val Arg Glu Thr Leu Lys
385                 390                 395                 400

Ala Val Gly Gln Leu Ala Pro Gly Thr Phe Gly Val Lys Arg Leu Val
            405                 410                 415

Phe His Asn Trp Val Lys Asp Glu Phe Ala Lys Gly Ala Trp Phe Phe
            420                 425                 430

Ser Arg Pro Gly Met Val Ser Glu Cys Leu Gln Gly Leu Arg Glu Lys
            435                 440                 445

His Gly Gly Val Val Phe Ala Asn Ser Asp Trp Ala Leu Gly Trp Arg
            450                 455                 460

Ser Phe Ile Asp Gly Ala Ile Glu Glu Gly Thr Arg Ala Ala Arg Val
465                 470                 475                 480

Val Leu Glu Glu Leu Gly Thr Lys Arg Glu Val Lys Ala Arg Leu
            485                 490                 495

<210> SEQ ID NO 4
<211> LENGTH: 8
<212> TYPE: PRT
<213> ORGANISM: Aspergillus niger

<400> SEQUENCE: 4

Leu Ile Lys Ala Ile Lys Gly Tyr
1               5

<210> SEQ ID NO 5
<211> LENGTH: 12
<212> TYPE: PRT
<213> ORGANISM: Aspergillus niger

<400> SEQUENCE: 5

Ile Ser Tyr Tyr Ile Gln His Asn Tyr Thr Cys Glu
1               5                   10

<210> SEQ ID NO 6
<211> LENGTH: 32
<212> TYPE: PRT
<213> ORGANISM: Aspergillus niger

<400> SEQUENCE: 6
```

```
Trp Gly His Ile Gln Ser Ile Ser Ser Arg Cys Arg Trp Arg Cys Ser
1               5                   10                  15

Ser Arg Glu Gln Arg Ile Ser Ala Pro Trp Arg Gln Cys Arg Thr Gln
            20                  25                  30

<210> SEQ ID NO 7
<211> LENGTH: 35
<212> TYPE: PRT
<213> ORGANISM: Aspergillus niger

<400> SEQUENCE: 7

Arg His Ser Ser Gly Arg Cys Arg Pro Glu Cys Arg Asp Leu Arg Arg
1               5                   10                  15

Cys Arg Tyr His Arg Gln Arg Tyr Arg Lys Cys Arg Trp Cys Cys Pro
            20                  25                  30

Arg Arg Arg
        35

<210> SEQ ID NO 8
<211> LENGTH: 9
<212> TYPE: PRT
<213> ORGANISM: Aspergillus niger

<400> SEQUENCE: 8

Gln His Arg Gly Ser Cys Arg Gly Gly
1               5

<210> SEQ ID NO 9
<211> LENGTH: 9
<212> TYPE: PRT
<213> ORGANISM: Aspergillus niger

<400> SEQUENCE: 9

Cys Arg Arg Ser Phe Arg Trp Met Val
1               5
```

DERACEMISATION OF AMINES

CROSS REFERENCE TO RELATED APPLICATIONS

This application is a continuation of U.S. patent application Ser. No. 11/685,939 filed on Mar. 14, 2007, now abandoned which is a divisional of U.S. patent application Ser. No. 10/508,356 filed Oct. 4, 2005, now U.S. Pat. No. 7,208,302 which was filed pursuant to 35 U.S.C. §371 as a United States National Phase Application of International Application No. PCT/GB2003/001198 filed Mar. 19, 2003 which claims priority from 0206415.2 filed Mar. 19, 2002 in Great Britain.

The present invention relates to a method for the deracemisation or chiral inversion of chiral amines by enzymatic treatment of a mixture of enantiomers. The method employs a stereoselective enzymatic conversion and either a non-selective or partially selective chemical or enzymatic conversion, simultaneously or sequentially. The invention also provides a method for selecting a suitable enzyme, particularly a suitable amine oxidase, and for the generation of novel enzymes suitable for use in the deracemisation method.

Enantiomerically pure chiral amines are valuable synthetic intermediates, particularly for the preparation of pharmaceutical target molecules. Traditionally, chiral amines have been obtained by separation methods such as diastereomeric crystallisation using a chiral acid to form a salt of one of the enantiomers, or by kinetic resolution of a racemate using an enzyme to selectively react one enantiomer allowing easier separation by physical methods such as solvent partitioning or chromatography (1). Whilst such methods can achieve high enantiomeric excess (e.e.), they can yield only a maximum of 50% of the racemic starting material as the required enantiomer. As with many chiral compounds, there is an increasing desire to develop synthetic strategies for amines that involve either asymmetric approaches or which combine resolution with racemisation of the undesired enantiomer, both of which can in principle deliver the product in 100% yield and 100% e.e. Asymmetric methods suggested to date include the use of transaminases for conversion of ketones to chiral amines (2, 3, 4). Furthermore the kinetic resolution of amines using lipases such as *Burkholderia plantarii* lipase (5, 6) or *Candida antarctica* lipase (7) has been combined with racemisation of the unreacted amine either by formation of an imine (5,6) or by transfer hydrogenation with Pd/C as the catalyst (7).

An alternative approach, which has been termed deracemisation, involves the stereoinversion of one enantiomer to the other e.g. using a cyclic oxidation-reduction sequence. To date it has been shown that such a system can be applied to the preparation of L-α-amino acids by the use of an enantioselective D-amino acid oxidase in combination with a non-selective reducing agent. The original work (8) reported the stereoinversion of D- to L-alanine, albeit in low yield, using sodium borohydride as the reducing agent. The instability of sodium borohydride at pH7 precludes its use on a practical scale, and recently we have shown that deracemisation of amino acids can be made more efficient by the use of more suitable reducing agents including sodium cyanoborohydride (13), ammonium formate with Pd/C and also borohydride complexes or amine:boranes (14). However, no-one to date has successfully applied a deracemisation method to amines.

SUMMARY OF THE INVENTION

The present invention provides a method for the deracemisation or chiral inversion (generally referred to herein as enantiomeric conversion) of chiral amines by treatment of a mixture of amine enantiomers with an enzyme capable of catalysing oxidation of the amine in a stereoselective manner and, subsequently or simultaneously, treating the mixture with a reducing agent. The method is applicable to mixtures of enantiomers in varying proportions, including racemic mixtures, and to conversion (epimerisation) of one single enantiomer to the other. For example the method is applicable to mixtures of R and S forms of an amine in a ratio of 1:1, 1:2, 1:5, 1:10, 2:1, 5:1, 10:1, 100:1 or other ratios. The product of the enantiomeric conversion is enriched in the desired enantiomer over the starting material i.e. the desired enantiomer is in enantiomeric excess. Preferably the product comprises a substantially pure single enantiomer. Thus, in preferred embodiments the enantiomeric conversion process of the invention is employed to convert a mixture of amine enantiomers into a composition consisting essentially of a single enantiomer, or is employed to convert one substantially pure amine enantiomer into the other, again in enantiomerically pure form.

The reducing agent may be partially stereoselective or non-stereoselective and may be a chemical reducing agent. Alternatively the reduction may be enzymatically catalysed. If a chemical reducing agent is to be employed, this may advantageously be selected from sodium borohydride, sodium cyanoborohydride, amine:borane complexes or a transfer hydrogenation reagent such as ammonium formate with Pd/C. If the stereoselective oxidation and non-stereoselective (or partially selective) reduction are performed sequentially, in an oxidation-reduction cycle, the cycle may be performed a plurality of times until the desired enantiomeric excess is achieved.

The enzyme capable of catalysing oxidation of the amine in a stereoselective manner may be a monoamine oxidase (MAO), particularly a microbial monoamine oxidase, but any amine oxidase enzyme may be employed. One MAO which may advantageously be employed in the method of the present invention is the *Aspergillus niger* monoamine oxidase or a variant thereof, for example a variant in which the enzyme differs from wild-type *A. niger* MAO by incorporation of one or more mutations, especially in the region of amino acids 25-265 and 334-350, particularly preferred are enzymes having a mutation at one or more of amino acids 259, 260, 336 and 348, more particularly the mutation N336S or the double mutation N336S, M348K.

The present invention also provides a method of directing the evolution of an originator enzyme by: a) mutating the originator enzyme to create at least one enzyme variant; b) screening said enzyme variant for activity against a homochiral substrate; and c) selecting one or more enzyme variants which show greater activity toward the homochiral substrate than does the originator enzyme. Optionally steps a), b) and c) may be repeated, using the enzyme variant selected in step c) as an originator enzyme. At appropriate stages, the enzyme variant(s) may be assayed against the opposite enantiomer of the substrate, or against a mixture of the substrate enantiomers, to confirm enantioselectivity. In particular embodiments, the originator enzyme is an oxidase which shows activity against amines, for example an amine oxidase, especially a monoamine oxidase. The substrate may be any chiral amine which can be oxidised to an imine, including cyclic secondary amines, for example amines of Formula I:

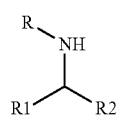

Formula I

In which:

a) R is H or $C_{1-4}$alkyl; R1 and R2 are independently selected from substituted or unsubstituted $C_{1-10}$alkyl, $C_{1-10}$alkenyl, $C_{1-10}$cycloalkyl, $C_{1-10}$heterocycle, $C_{1-10}$aryl, $C_{1-10}$heteroaryl, $C_{1-4}$alkyl-aryl, $C_{1-4}$alkyl-heteroaryl, $C_{1-4}$alkyl-$C_{1-6}$cycloalkyl and $C_{1-4}$alkyl-$C_{1-6}$ heterocycle; or b) R is H or $C_{1-4}$alkyl, R1 and R2 together form a substituted or unsubstituted $C_{1-10}$cycloalkyl ring system or $C_{1-10}$aryl ring containing one or more heteroatoms; or c) R and R1 together form a substituted or unsubstituted $C_{1-10}$cycloalkyl or $C_{1-10}$aryl ring system which may contain one or more heteroatoms and R2 is defined as in a) above.

As used herein, the terms "halo" or "halogen" refer to fluorine, chlorine, bromine and iodine.

As used herein, the term "alkyl" refers to a straight or branched hydrocarbon chain containing the specified number of carbon atoms. For example, $C_1$-$C_3$alkyl means a straight or branched hydrocarbon chain containing at least 1 and at most 3 carbon atoms. Examples of alkyl as used herein include, but are not limited to; methyl, ethyl, n-propyl, i-propyl.

As used herein, the term "cycloalkyl" refers to a fully saturated hydrocarbon ring containing the specified number of carbon atoms. The term "cycloalkyl" encompasses single and bicyclic ring structures. Examples of cycloalkyl as used herein include, but are not limited to cyclohexyl, cyclopropyl.

As used herein, the term "aryl" refers to an unsaturated which may be saturated or unsaturated hydrocarbon ring containing the specified number of carbon atoms. The term "aryl" encompasses single and bicyclic ring structures. Examples of cycloalkyl as used herein include, but are not limited to phenyl, naphthyl.

Where cycloalkyl or aryl ring systems contain one or more heteroatoms, these are selected from N, S or O, preferably N. Thus, the terms "heterocyclic" and "heteroaryl" refer to cycloalkyl and aryl groups, respectively, which contain up to three heteroatoms selected from N, S or O, preferably N.

Where one or more of R, R1 and R2, or a ring formed therebetween, are substituted, one to three substituents may be present and are selected from halogen, hydroxy, $C_{1-3}$alkyl, $C_{1-3}$alkenyl, $C_{1-3}$alkoxy, nitro, nitrile and $CONH_2$.

Conveniently, the target substrate can be used for evolution of enzymes with improved activity and enantioselectivity for that particular substrate.

The invention therefore provides a method of improving the catalytic activity, and optionally also the enantioselectivity, of an amine oxidase, especially a monoamine oxidase, by directed evolution comprising mutation of the enzyme and selection of a mutant having improved activity against a homochiral substrate. The use of an enzyme variant, selected by such a method, in a method for the deracemisation or epimerisation of amines is also provided.

The wild-type amino acid sequence of *A. niger* MAO is set out in SEQ. ID No. 1. In one embodiment the invention provides a variant of the *A. niger* MAO in which the enzyme differs from wild-type *A. niger* MAO in the region of amino acids 334-350, particularly amino acid 336 and/or amino acid 348, more particularly by incorporation of the mutation N336S or the double mutation N336S, M348K. The invention thus provides a variant of the *A. niger* MAO having the amino acid sequence set out in SEQ. ID No. 2 and, in a further embodiment, a variant of the *A. niger* MAO having the amino acid sequence set out in SEQ. ID No. 3.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

A chiral compound will have two or more enantiomers which are stereochemically dissimilar. A composition which contains more than one enantiomer of a chiral compound is referred to as a "racemic mixture" if it contains the enantiomers in equal or substantially equal amounts. By contrast a composition is "homochiral", "enantiomerically pure" or a "substantially pure single enantiomer" if it contains a single enantiomer, substantially free of the corresponding enantiomer, or consists essentially of one enantiomer in the absence of the other. By 'substantially free' is meant no more than about 5% w/w of the corresponding enantiomer, particularly no more than about 3% w/w, and more particularly less than about 1% w/w is present. "Enantioselective" and "stereoselective" are used herein interchangeably and refer to the tendency of a reaction to favour one enantiomer of a chiral compound over the other. "Partially stereoselective" (or "partially enantioselective"), "non-enantioselective" etc. shall be understood accordingly.

The invention will now be described in more detail, with reference to the accompanying drawings and sequence listings, in which:

FIG. 3 shows the results of 27 enzymes selected from the detection assay of FIG. 2, assayed against L-AMBA and D-AMBA;

SEQ ID NO:1 shows the amino acid sequence of the wild-type *Aspergillus niger* monoamine oxidase enzyme (NB we found the sequence to differ by 4 amino acids from that reported by Schilling & Lerch (10,11). These changes most likely represent errors in the original DNA sequencing; two of these differences are also noted by Sablin (12).);

SEQ ID NO:2 shows the amino acid sequence of a variant monoamine oxidase enzyme generated by directed evolution in the following Examples. The mutation N336S is shown in bold face type and underlined;

SEQ ID NO: 3 shows the amino acid sequence of a variant monoamine oxidase enzyme generated by site directed mutagenesis of the N336S mutant enzyme of SEQ ID NO: 2. The mutations N336S and M348K are shown in bold face type and underlined.

Figure 1:
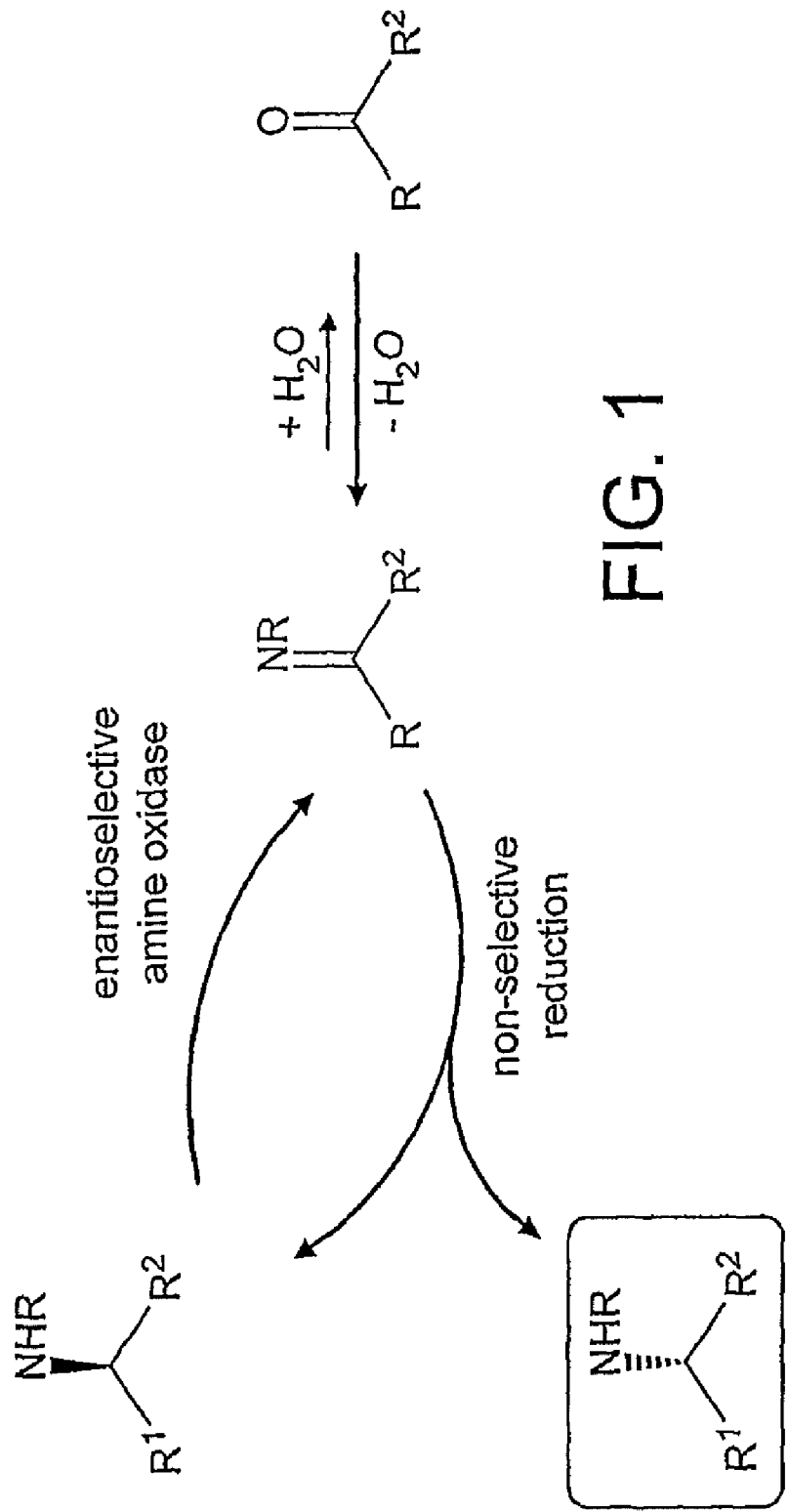
FIG. 1 shows the reaction scheme for the oxidation-reduction cycle which results in deracemisation.

Herein we report a significant new extension of deracemisation, by applying the method for the first time to the deracemisation of chiral amines. The reaction follows the general scheme shown in FIG. 1. One enantiomer is converted to the other because the enzyme reacts preferentially with one of the two chiral forms, leaving the other unreacted. The enzyme reaction produces the achiral imine, which does not have a chiral centre at the nitrogen-bearing carbon. Non-selective reduction of the imine results in the creation of a 1:1 mixture of amine enantiomers (if a partially selective reducing agent were employed, an unequal mixture of amine enantiomers would be formed). As this process is allowed to undergo a number of cycles, the amine approaches enantiomeric purity (assuming a sufficiently enantioselective amine oxidase). The yield can approach 100% If the imine can be efficiently reduced before undergoing hydrolysis to the ketone.

Amine oxidases have been classified into two groups, namely Type I (Cu/TOPA dependent) and Type II (flavin dependent) (15). In the catalytic cycle of the Type I enzyme, the intermediate imine remains covalently bound to the protein, which mitigates against intervention at this stage in the reaction to reduce the imine back to the amine. The Type II enzymes have been extensively studied from mammalian sources (9), however microbial sources of Type II enzymes are poorly documented and indeed at the outset of our work there were no reports of enantioselective transformations. Schilling et al., (10, 11) reported the cloning and expression of a Type II monoamine oxidase from *Aspergillus niger* (MAO-N) and subsequently Sablin et al., (12) purified the enzyme to homogeneity and carried out substrate specificity and kinetic studies. The enzyme was reported to have high activity towards simple aliphatic amines (e.g. amylamine, butylamine) but was also active, albeit at a lower rate, towards benzylamine.

Our studies have revealed that the *A. niger* MAO-N enzyme possesses very low, but measurable activity towards L-α-methylbenzylamine with even slower oxidation of the D-enantiomer. Thus the enzyme is partially enantioselective. We have carried out in vitro evolution (16, 17) to generate new amine oxidase enzymes having improved catalytic activity and enantioselectivity over the wild-type *A. niger* MAO-N enzyme. We have also demonstrated the applicability of the evolved mutants in deracemisation reactions.

To generate a large library of enzyme variants we used a mutator strain for random mutation of a plasmid containing an insert encoding the wild-type *A. niger* amine oxidase enzyme. The *E. coli* XL1-Red mutator strain (Stratagene) has been employed previously for in vitro evolution experiments and has the advantage that all parts of the plasmid are subject to mutation (cf. error prone PCR where only the gene of interest is mutated) which can result in improved production of enzyme as well as changes to enzyme activity and/or specificity. By carrying out multiple cycles with the mutator strain followed by transformation of the plasmid library into *E. coli* BL21 cells, we were able to generate a library of around $10^6$ variants.

Having generated the mutant enzymes, we assayed them for amine oxidase activity. Amine oxidases are typical of all members of the oxidase family in that they evolve hydrogen peroxide as a by-product. Many of the reported assays for oxidase activity exploit the production of hydrogen peroxide, especially coupled with peroxidase in the presence of a substrate that upon oxidation yields a highly coloured product. We first used aminoantipyrine/tribromohydroxybenzoic acid as the substrate for the peroxidase, which yielded distinct pinkish-red colonies which could be easily visualised. However the coloured product is relatively soluble and hence colour from the active colonies rapidly diffused giving high background intensity. This problem was overcome by switching to 3,3'-diaminobenzadine (DAB) as the substrate which gave rise to a dark pink, insoluble product resulting in both very high definition and contrast of the active colonies. It should be noted that this high-throughput screen should be generally applicable to other oxidase enzymes in addition to amine oxidases.

Figure 2:
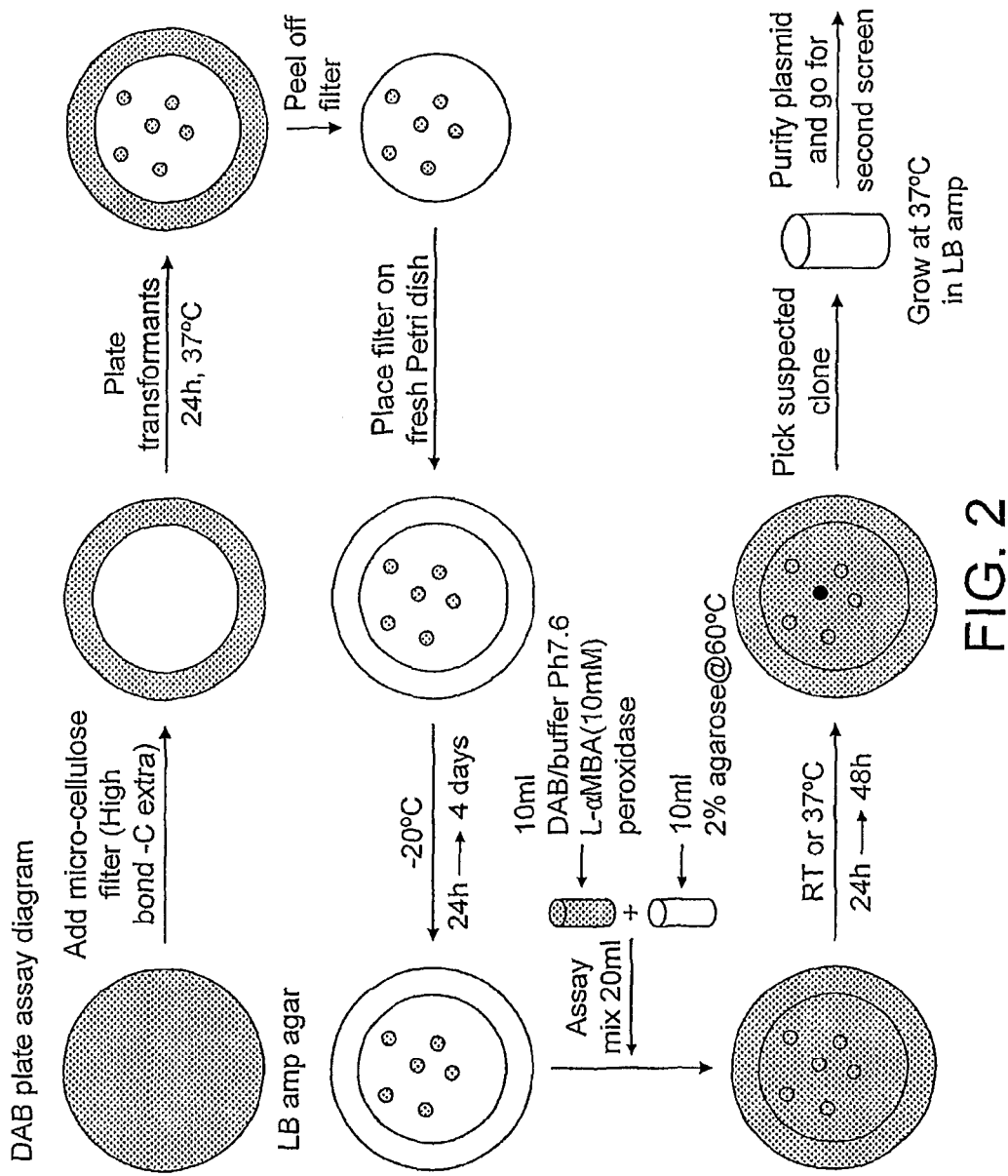
FIG. 2 shows diagrammatically the assay used to detect enzymes having the desired enantioselective amine oxidase activity.

The library was plated out directly onto nitro-cellulose filters on agar-plates (around 3,000 colonies per plate) and a sub-set of the plates taken through the screening protocol (see FIG. 2). Each filter was transferred to a petri-dish and stored at −20° C. for 24-72 h in order to partially lyse the cells. Thereafter, each plate was treated with a cocktail containing both the assay mixture and also 2% agarose at 60° C. The plates were incubated at 37° C. for 24-48 h after which they was inspected for positive clones which were then removed and plated at higher dilution to isolate pure colonies.

The result of screening a subset (ca. 150,000 clones) of the initial library led to the identification of 35 clones with improved activity towards L-AMBA compared to the wild-type enzyme. Each of these clones was grown on a small scale and assayed against both L- and D-AMBA as cell-free extracts resulting in the best 27 clones which were selected for further study. Each of these 27 were assayed against L-AMBA and D-AMBA, the results of which are presented in FIG. 3. Finally, the mutant enzyme clone which showed greatest improvement over the wild-type enzyme in terms of its selectivity, and activity, towards L- versus D-AMBA was selected for more detailed examination. Further mutation was then introduced to boost expression.

It is known that the codons used in the DNA and RNA to encode amino acids show a certain redundancy. Thus, a given amino acid may be coded for by more than one 3-base codon. However, a given organism may more commonly use one of the alternative codons than the other(s) for a given amino acid. This has implications if a heterogeneous nucleic acid is introduced into a host organism for expression. Sometimes the codons used by the originator organism are the "less preferred" codons for the host, which can result in difficulties in expression such as a reduced level of expression. Similarly, certain amino acids may be less commonly represented in the proteome of one organism when compared to another. It may sometimes possible to boost the levels of heterologous expression in a host cell by using an alternative nucleic acid sequence in which codons and/or amino acids which are less preferred by the host are exchanged for more preferred alternatives. The present invention provides an isolated nucleic acid which encodes a monoamine oxidase enzyme which is a variant of the *A. niger* MAO in which the codons for R259 and R260 are optimised for expression in a heterogeneous host cell. More particularly, when the expression of the MAO is intended to take place in *E. Coli*, the arginine amino acids at these positions are replaced by alternative amino acids of a similar charge and size. These mutations may in addition to mutations which alter the catalytic activity and/or enantioselectivity of the mutant enzyme. In a further embodiment, we provide an enantioselective monoamine oxidase enzyme which is a variant of the *A. niger* MAO and which differs from wild-type *A. niger* monoamine oxidase by incorporation of the mutations N336S and one or more of M348K, R259L and R260L.

The mutant N336S identified below may be taken as the basis for "hotspot" mutation in which further mutations are introduced in the amino acids surrounding position 336. Mutations may be made by site-directed mutagenesis, by the construction of chimeric recombinant enzymes using a "cut and paste" methodology employing restriction enzymes, or by other means well known to workers skilled in the art. This method is used to identify further mutants with enhanced activity over the N336S mutant, such as the N336S, M348K double mutant identified herein.

EXAMPLE 1

Preparation of Mutated Plasmid DNA Library by *E. coli* XL1-Red Mutator Strain The MAO gene from *Aspergillus niger* cloned in pET3a was obtained from B. Schilling (11). The gene was amplified by pfu Turbo DNA polymerase (Stratagene) using primers designed according to *E. coli* codon usage. The PCR product was subcloned into the pET16b vector (Novagen). This construct (MAOpET16b) was submitted for mutagenesis by the *E. coli* XL1-Red mutator strain.

*E. coli* XL1-Red mutator strain competent cells were obtained from Stratagene. Competent cells were transformed as described in the Stratagene protocol. 700 µl of transformed cell suspension (Transformation 1) was inoculated in 20 ml of LB medium (tryptone, 10 g/L; yeast extract, 5 g/L; NaCl, 10 g/L; pH7) with ampicillin (100 µg/ml; LB Amp) and grown for 18 h in a 50 ml Falcon tube in an incubator shaker at 37° C. These growing conditions were used throughout the experiment.

20 µl of growing culture was inoculated in 10 ml of fresh LB Amp and grown for 24 h. The plasmid was purified (Qiagen Plasmid DNA Miniprep Kit) from 1 ml culture (pMAO2) and used for the second transformation (Transformation II) of the mutator strain. The total transformed cell suspension was inoculated in 10 ml of LB Amp and grown for 24 h. The plasmid was purified from 1 ml of culture (pMAOretr1.1). 100 µl of Transformation II growing culture was used to inoculate 10 ml LB Amp. The culture was grown for 24 h, the plasmid purified (pMAOretr1.2) and used for Transformation III. Total transformed cell suspension (1 ml) was inoculated in 10 ml LB Amp, grown for 24 h and the plasmid purified (pMAOretr2.1). 100 µl of Transformation III growing culture was used to inoculate the next 10 ml of LB Amp, grown for 24 h and the plasmid purified from 1 ml culture (pMAOretr2.2) and used for Transformation IV. Total suspension of transformed cells (1 ml) was used to inoculate 10 ml of LB Amp, grown for 24 h and the plasmid purified from 1 ml culture (pMAOretr3.1). 100 µl of Transformation IV growing culture was used to inoculate fresh 10 ml LB Amp, grown for 24 h and the plasmid purified (pMAOretr3.2).

Collected pools of mutated plasmid DNA (pMAOretr2.2, pMAOretr3.1, pMAOretr3.2) were used to transform *E. coli* BL21(DE3) to express mutated MAO genes and detect activity towards L-α-methylbenzylamine (L-AMBA) oxidation.

EXAMPLE 2

Screening for MAO Mutants

The plate assay method (FIG. 2) was used to identify MAO mutants with activity towards L-AMBA. More specifically, *E. coli* BL21(DE3) transformants (2500 colonies per plate) were plated on HiBond-C Extra (Amersham Pharmacia) membrane placed on an LB Amp agar plates and incubated for 24 h at 37° C. Membranes containing the colonies were pulled from the plates, kept at −20° C. for 24 h and incubated with assay mixture at room temperature for 24 h.

Assay Mixture:
1 tablet of DAB (3,3'-diaminobenzidine, Sigma, D-4418)
1 ml of K phosphate buffer (1M, pH7.6)
30 µl L-AMBA (10 mM)
30 µl horseradish peroxidase (Sigma) 1 mg/ml
10 ml 2% agarose (Bio-Rad)
Water up to 20 ml Positive clones were subjected to a second round of screening (100-200 colonies per plate) to confirm activity.

EXAMPLE 3

Activity Studies a) Clone Selection 27 positive clones identified in the plate assay as having improved activity towards L-AMBA compared to the wild-type enzyme were grown on a small scale and assayed against both L- and D-AMBA. 10 ml LB Amp was inoculated with a single colony of *E. coli* BL21(DE3) transformed with the protein expression vector pET16b harbouring the gene of interest and cultured in a 50 ml Falcon tube with agitation for 24 h. At the end of incubation 1 ml of cell culture was centrifuged, the pellet was resuspended in 1 ml of 25 mM potassium phosphate buffer pH7.6 and 0.1 ml was used to perform a hydrogen peroxide formation assay using both L- and D-AMBA as substrates.

Assay Mixture: (Manfred Braun et al, *Applied Microbiology and Biotechnology* (1992) 37:594-598)
5 ml phosphate buffer (1M, pH7.6)
500 µl 2,4,6-tribromohydrobenzoic acid (2% in DMSO),
37.5 µl 4-aminoantipurine (1M)
32.5 µl L or D-AMBA (final concn 5 mM)
Water up to 50 ml
To 895 ul Assay Mixture was Added:
5 µl HRP (Sigma, P6782) (1 mg/ml)

Sample (100 µl) was added and absorbance at 510 nm measured after 24 hours against a control without sample. The absorbance results are shown in FIG. 3.

Several of these 27 clones appear to be expression mutants, as they demonstrate increased protein expression when visualised on polyacrylamide gels (data not shown). The plasmid of the best mutant identified, which appeared not to have increased expression but which showed greatest improvement over the wild-type enzyme in terms of its selectivity, and activity, towards L- versus D-AMBA, was grown on a larger scale and the enzyme purified. The wild-type enzyme was also purified by the same protocol and the two enzymes compared for substrate specificity and enantioselectivity.

The mutated gene was also sequenced and the sequence is shown in SEQ ID NO: 2. There was a single amino acid change from the wild-type enzyme with serine replacing asparagine at position 336.

b) Growth and Comparison of Mutant and Wild-Type Enzymes

Growth and Purification of MAO Mutant Expressed in *E. coli* BL21(DE3)

LB medium (6×300 ml) containing ampicillin (100 µg·ml$^{-1}$) in 1 L baffled flasks was inoculated with a single colony of monoamine oxidase mutant from an LB agar plate. Cultures were incubated at 30° C. for 22 hours (OD$_{600}$~3.6) then harvested and washed with phosphate buffer (50 mM, pH 8) to yield a yellow-brown pellet (11.2 g).

The pellet was resuspended in Tris/HCl buffer (25 mM, pH 7.8, 30 ml) and sonicated on ice (30 s on, 30 s off for 10 minutes). The suspension was then centrifuged (20,000 rpm, 4° C.) until clear supernatant was obtained and the supernatant dialysed against Tris/HCl buffer (25 mM, pH 7.8). The cell free extract was filtered through 0.45 µm sterile membrane and chromatographed on a QSepharose anion exchange column. Fractions were assayed using colorimetric hydrogen peroxide based assay and active fractions were stored at −80° C. The active fraction has a protein content of 1 mg·ml$^{-1}$, and a specific activity of 0.193 U·mg$^{-1}$ against amylamine.

Chromatography Conditions:
Column=HiFlow QSepharose 26/10
Buffer A=Tris/HCl (25 mM, pH 7.8)

Buffer B=Tris/HCl (25 mM, pH 7.8)+1 M NaCl
Flow rate=4 ml·min$^{-1}$
Fraction collect=10 ml
Column wash=2 CV 100% buffer A
Elution=10 CV 100% buffer A to 100% buffer B
Column clean=4 CV 100% buffer B
Assay Mixture:
5 ml phosphate buffer (1 M, pH 7.6)
500 µl 2,4,6-tribromo-3-hydroxybenzoic acid (2% in DMSO)
37.5 µl 4-aminoantipyrine (1.5 M)
30 µl amine substrate (final concentration 0.015-5 mM)
44.4 ml water
Assay Conditions:
990 µl assay mixture
5 µl horse radish peroxidase (1 mg·ml$^{-1}$)
10 µl enzyme The spectrophotometer was blanked against assay mixture and HRP. Enzyme was added and the absorbance at 500 nm measured at 3 s intervals for a 10 minute period.

Results:

|  | Wild-type Enzyme | | Mutant Enzyme | |
| --- | --- | --- | --- | --- |
| Substrate | $K_m$ mM | $k_{cat}$ min$^{-1}$ | $K_m$ mM | $k_{cat}$ min$^{-1}$ |
| L-AMBA | ND | 0.17 | 0.4 | 8.0 |
| D-AMBA | ND | 0.01 | ND | 0.08 |
| benzylamine | ND | 371 | ND | 196 |
| amylamine | — | 1000 | 0.4 | 116 |

The $K_m$ values were calculated using 'KaleidaGraph for Windows' (Synergy Software). For calculation of the $k_{cat}$, the active enzyme concentration was determined by estimating the FAD content from the absorbance at 458 nm using an extinction coefficient of 11 mM$^{-1}$ cm$^{-1}$ (see ref 12).

The data reveal that the activity of the mutant amine oxidase towards L-AMBA (kcat=8.0 min-1) is 47 fold higher than the wild-type (kcat=0.17 min-1). Moreover the selectivity of the mutant for the L-enantiomer versus D-AMBA (ca. 100:1) has also been increased relative to the wild type enzyme (ca. 17:1). Thus the outcome of the in vitro evolution experiments has been to simultaneously improve both the enantioselectivity and catalytic activity of the enzyme. For comparison, the activity towards the best substrate for the wild-type enzyme, namely amylamine, and also benzylamine, is presented. The substantial improvement in activity and selectivity of the mutant was confirmed by chiral HPLC (Chiralcel CrownPak CR+) in which after 24 h complete oxidation of the L-enantiomer was apparent whereas there was no detectable conversion of the D-enantiomer.

EXAMPLE 4

Deracemisation Reaction

Using DL-AMBA as the substrate, in the presence of the mutant MAO-N, a range of reducing agents were screened (sodium borohydride, catalytic transfer hydrogenation, amine:boranes). This screen identified ammonia:borane as the optimal reagent which gave a 77% yield of D-AMBA with an enantiomeric excess=93%. Greater optical purities of the product (up to 99% e.e.) could be achieved although at the expense of yield.

More specifically, MAO mutant N336S (100 µl of 0.193 U·ml$^{-1}$=0.02 U) was added to a solution of DL-AMBA (0.13 µl, final concentration=0.8 mM) and ammonia-borane complex (10 µl of 4M solution, final concentration=80 mM, 100 eq) in phosphate buffer (400 µl, 20 mM, pH8). A 10 µl aliquot was diluted in 990 µl perchloric acid, pH 1.5 and analysed by HPLC. The reaction mixture was incubated at 30° C. and the reaction monitored by HPLC at regular intervals until no further reaction was observed.

Yield: D-AMBA=77%, e.e.=93%
Analytical conditions: Column=Chiralcel CrownPak CR+
Mobile phase=100% perchloric acid, pH 1.5
Flow rate=0.8 ml·min$^{-1}$
Detection=200 nm
Temperature=25° C.
r.t. (L-AMBA)=12.8 min
r.t. (D-AMBA)=16.5 min

EXAMPLE 5

Stereoinversion Reaction

We also carried out the stereoinversion of L- to D-AMBA (18% yield, 99% e.e.) and showed that under identical conditions there was no conversion of D- to L-AMBA.

More Specifically, MAO mutant N336S (100 µl of 0.193 U·ml$^{-1}$=0.02 U) was added to a solution of L-AMBA (0.13 µl, final concentration=0.4 mM) and ammonia-borane complex (10 µl of 4M solution, final concentration=80 mM, 200 eq) in phosphate buffer (400 µl, 20 mM, pH8). A 10 µl aliquot was diluted in 990 µl perchloric acid, pH 1.5 and analysed by HPLC. The reaction mixture was incubated at 30° C. and the reaction monitored by HPLC at regular intervals until no further reaction was observed.

Yield D-AMBA=18%, e.e. >99%:
NB: no reaction was observed after 24 hours when D-AMBA was used as substrate under identical reaction conditions.

Analytical conditions: Column=Chiralcel CrownPak CR+
Mobile phase=100% perchloric acid, pH 1.5
Flow rate=0.8 ml·min$^{-1}$
Detection=200 nm
Temperature=25° C.
r.t. (L-AMBA)=12.8 min
r.t. (D-AMBA)=16.5 min Analysis of the HPLC chromatograms suggests that the yield in the deracemisation reactions is prevented from reaching 100% due to the formation a by-product with longer retention time as the reaction progresses. We are currently optimising the deracemisation protocol to achieve the exquisite levels of yield and selectivity previously demonstrated for the deracemisation of α-amino acids.

Abbreviations:
MAO—monoamine oxidase.
AMBA—α-methylbenzylamine
TBHBA—2,4,6-tribromo-3-hydroxybenzoic acid
AAP—4-aminoantipyrine
HRP—horse radish peroxidase type VI from bovine liver
LB—Lubria Bertani
r.t.—retention time

EXAMPLE 6

Substrate Specificity of the N336S Mutant Enzyme

The activity of the mutant enzyme described above was studied in relation to a variety of amine substrates. Assay conditions were essentially as set out in Example 3. The substrates tested were:

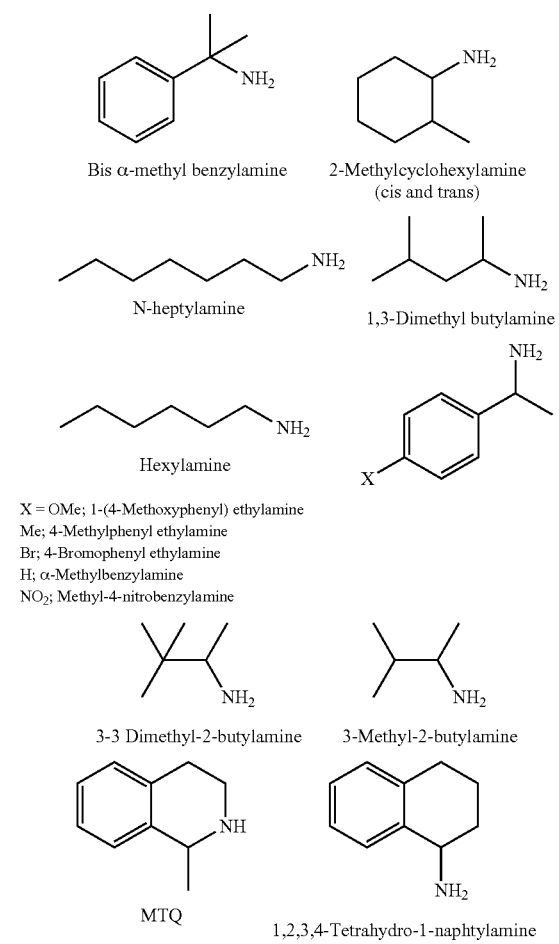

Results:

| Sample | Relative Rate |
| --- | --- |
| (S)-α Methylbenzylamine | 1 |
| (R)-α Methylbenzylamine | * |
| (rac)-α Methylbenzylamine | * |
| (S)-4-Methylphenylethylamine | 0.28 |
| (R)-4-Methylphenylethylamine | * |
| (S)-α-Methyl-4-nitrobenzylamine | 0.91 |
| (R)-α-Methyl-4-nitrobenzylamine | 0.06 |
| (S)-4-Bromo-α-phenylethylamine | 0.24 |
| (R)-4-Bromo-α-phenylethylamine | * |
| (rac)-4-Bromo-α-phenylethylamine | * |
| (S)-1-4-Methoxyphenylethylamine | 0.81 |
| (R)-1-4-Methoxyphenylethylamine | 0.13 |
| (S)-MTQ | 0.67 |
| (R)-MTQ | * |
| (rac)-MTQ | 0.13 |
| (S)-3-Methyl-2-butylamine | 5.4 |
| (R)-3-Methyl-2-butylamine | * |
| (S)-3-3-Dimethyl-2-butylamine | 1.4 |
| (R)-3-3-Dimethyl-2-butylamine | * |
| 2-Methylcyclohexylamine | 0.43 |
| N-heptylamine | 12.1 |
| N-amylamine | 25.2 |
| Hexylamine | 18.6 |
| Bis(α-methyl)benzylamine | * |
| 1,3-Dimethylbutylamine | 1.8 |
| 1,2,3,4-Tetrahydro-1-naphthylamine | 0.13 |

* No measurable rate

EXAMPLE 7

Creation of a Further Mutant Clone

The first published sequence of wild-type *A. niger* monoamine oxidase showed a lysine at position 348. Some of the mutant enzymes generated above and initially tested in Example 3(a) were thought to be double mutants because they had a methionine at this position. However, when the wild-type sequence was checked (resequenced), the wild-type amino acid at position 348 was shown to be methionine (as set out in SEQ ID NO:1). In order to elucidate the impact (if any) of a mutation at this site, site-directed mutagenesis was performed on the wild-type enzyme to introduce the M348K mutation. It was noted that the identity of the amino acid at this position influenced the efficiency of expression, with lysine giving rise to increased expression without altering the catalytic activity of the enzyme (absolute activity in U/ml is greater than wild type, but correction for the amount of protein gives a value of $k_{cat}$ which is the same as for the wild-type enzyme). Site directed mutagenesis was then performed upon the N336S mutant described above to generate a second mutation (M348K), thus combining the catalytic enhancement of the N336S mutation with an increase in expression. The amino acid sequence of the double mutant is set out in SEQ ID NO: 3.

EXAMPLE 8

Substrate Specificity of the N336S, M348K Mutant Enzyme

Figure 4:
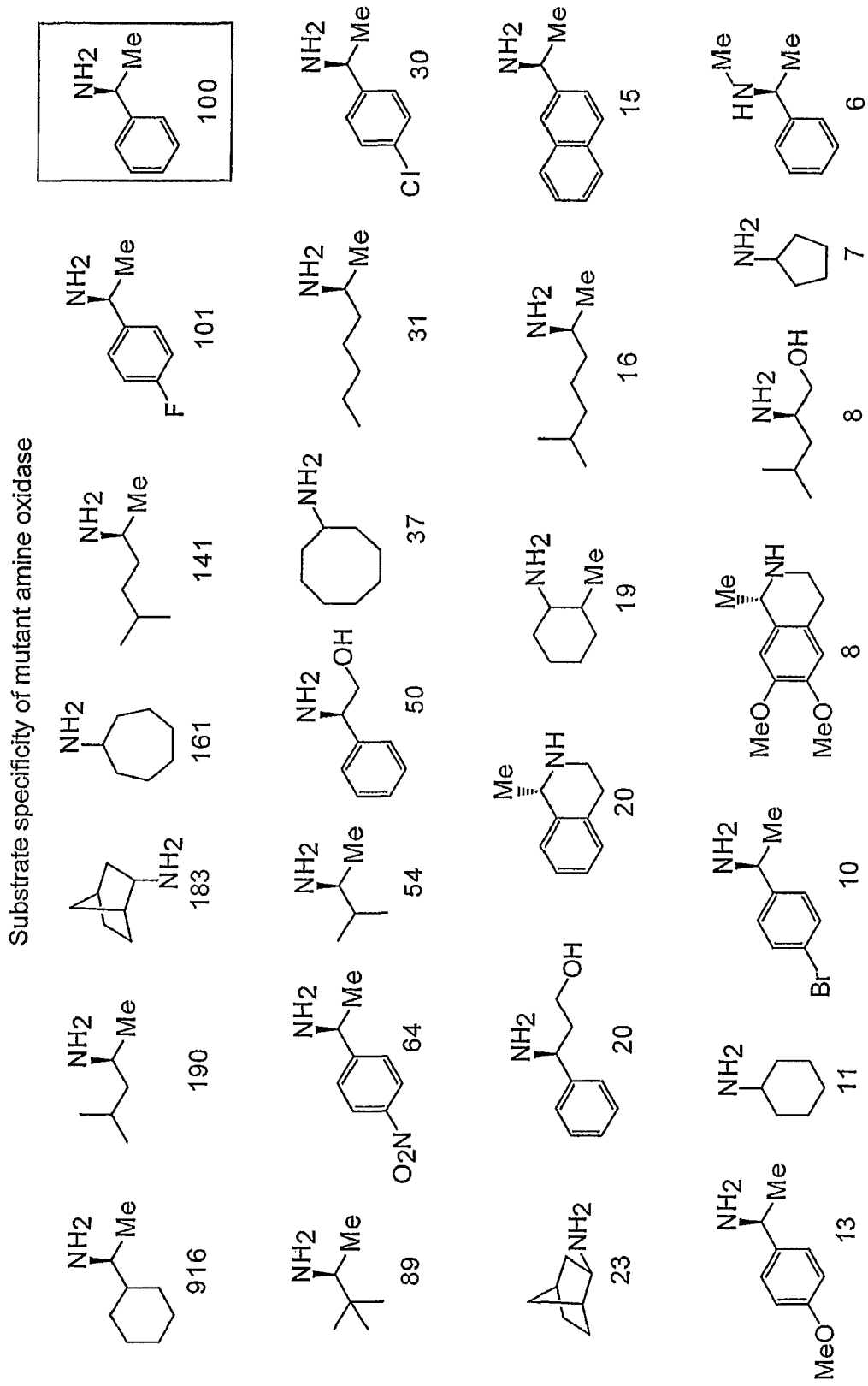
FIG. 4 shows the substrate specificity of the N336S, M348K mutant *A. niger* monoamine oxidase.
Figure 5:
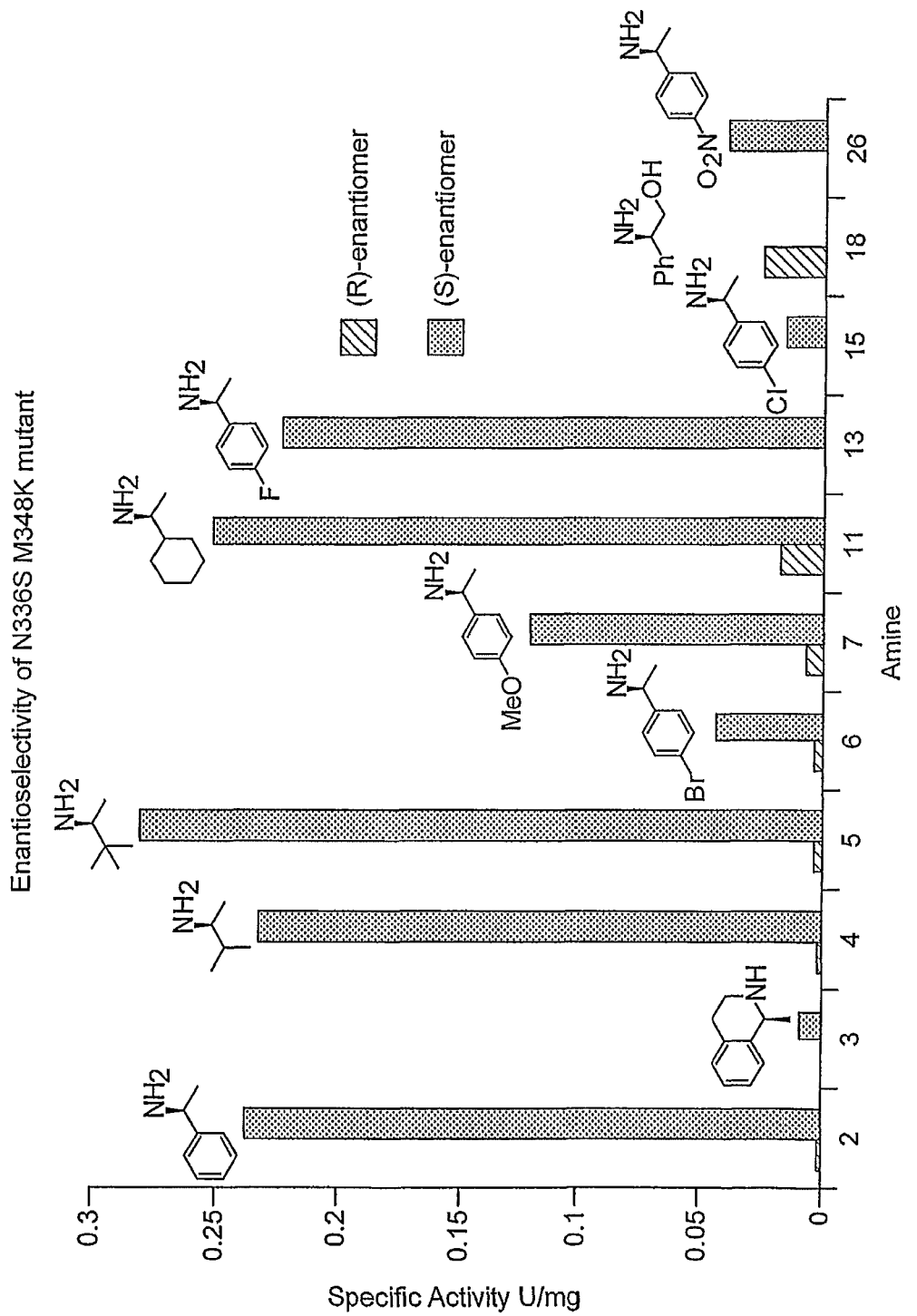
FIG. 5 shows the enantioselectivity of the N336S, M348K mutant *A. niger* monoamine oxidase.

The activity of the double mutant enzyme described above was studied in relation to a variety of amine substrates. Assay conditions were essentially as set out in Example 3. The substrates tested and the relative rates of conversion (compared to L-AMBA set at 100) are shown in FIG. 4. For some substrates, both enantiomers were tested as substrates. The enzyme appears to demonstrate enantioselectivity in every case, with activity against the opposite enantiomer being undetectable in several cases (the enantioselectivity data is shown in FIG. 5).

EXAMPLE 9

Application of Expression Mutant R260K

The mutation R260K was found to be in low occurrence codon for arginine. The sequencing results revealed that all of the "expression" mutants had the same mutation at position 260 wherein arginine was replaced by lysine.

The wild type MAO-N amino acid sequence has two arginines at position 259 and 260 both encoded by the codon (AGG), which has a low occurrence in *E. coli* genes (4%). Lysine and arginine are both basic amino acids and hence replacement of one by the other should not affect the charge of the protein, however the replacement of a low frequency codon for Arg AGG (4%) by a high frequency codon for Lys AAG (22%) results in improved protein expression in *E. coli*. Thus we decided to replace the codons of both Arg 259 and Arg 260 with the codon CGT (38%) by site directed mutagenesis to evaluate the effect upon the expression level of MAO-N. An alternative approach would be to create a "silent" mutation by altering the AGG codon to a different codon which still encodes arginine (AGA, CGT, CGC, CGA, CGG).

MAO WT and MAOArg259/260 were partially purified from recombinant *E. coli* BL21(DE3) harbouring a pET16b carrying the corresponding mao-n gene. Cell free extracts were prepared by sonication and the specific activities of MAO WT and MAOArg259/260 towards AA were measured for both the soluble and insoluble fractions. (Table 3)

TABLE 3

Specific activities towards AA in partially purified MAO WT and MAOArg259/260 towards amylamine.

| Enzyme | Protein concentration mg · ml$^{-1}$ | Soluble fraction U · mg$^{-1}$ | Insoluble fraction U · mg$^{-1}$ | Total activity U |
|---|---|---|---|---|
| MAO WT | 1.18 | 0.23 | 0.33 | 0.57 |
| MAOArg259/260 | 1.30 | 0.46 | 0.56 | 1.2 |

To confirm the increased level of the R260K mutant expression, Cell free extracts of MAO WT, mutant 4 (R260K) and MAOArg259/260 were obtained and assayed towards L-AMBA. This was achieved by incubating 50 μl of each sample for 240 minutes and specific activities were determined. (Table 4)

TABLE 4

| Enzyme | ΔAbs 510 nm | Soluble fraction U · mg$^{-1}$ |
|---|---|---|
| MAO WT | 0.06 | $3.6 \times 10^{-5}$ |
| MAOArg259/260 | 0.12 | $7.0 \times 10^{-5}$ |
| MAO mutant (R260K) | 0.16 | $5.7 \times 10^{-5}$ |

In conclusion, we have significantly extended the deracemisation strategy by applying the method for the first time to the deracemisation of chiral amines. In so doing we have successfully achieved the 'directed evolution' of an enzyme in order to meet the specific requirements of a novel biotransformation. Another interesting aspect of the present work is the identification of a highly enantioselective mutant by using a single enantiomer substrate in the screen (L-AMBA). There has been much discussion concerning the need for truly enantioselective screens in which racemates are used, thereby mimicking the real-life situation found in a kinetic resolution in which the two enantiomers compete for the enzyme. It may be that if one is able to screen truly large and diverse libraries of variant genes (e.g. 10$^6$) then it is possible to select for enantioselectivity in the manner described herein, using inherently simpler screens.

The application of which this description and claims form part may be used as a basis for priority in respect of any subsequent application. The claims of such subsequent application may be directed to any feature or combination of features described herein. They may take the form of product, composition, process or use claims and may include, by way of example and without limitation, one or more of the following claims:

REFERENCES (1) L. E. Iglesias, V. M. Sanchez, F. Rebolledo and V. Gotor, *Tetrahedron: Asymmetry* (1997) 8, 2675-2677.
(2) J. S. Shin, B. G. Kim, A. Liese and C. Wandrey, *Biotechnol. Bioeng.* (2001) 73 179-187;
(3) G. Matcham, M. Bhatia, W. Lang, C. Lewis, R. Nelson, A. Wang and W. Wu, *Chimia* (1999) 53, 584-589;
(4) J. S. Shin, B. G. Kim, *Biotechnol. Bioeng.*, (1999) 65, 206-211.
(5) G. Hieber and K. Ditrich, *Chimica Oggi* (2001) 19, 16-20;
(6) F. Balkenhohl, K. Ditrich, B. Hauer and W. Ladner, *J. Prakt. Chem.* (1997) 339, 381.
(7) M. T. Reetz and K. Schimossek, *Chimia*, (1996), 50, 668-669.
(8) E. W. Hafner and D. Wellner, *Proc. Nat. Acad. Sci.* (1971) 68, 987.
(9) R. B. Silverman, J. M. Cesarone and X. Liu, *J. Am. Chem. Soc.* (1993) 115, 4955.
(10) B. Schilling and K. Lerch, *Biochim. Biophys. Acta.* (1995), 1243, 529.
(11) B. Schilling and K. Lerch, *Mol. Gen. Genet.* (1995) 247, 430.
(12) S. O, Sablin, V. Yankovskaya, S. Bernard, C. N. Cronin and T. P. Singer, *Eur. J. Biochem.* (1998) 253, 270.
(13) T Beard and N J Turner *Chem. Commun.* 2002 in press.
(14) F R Alexandre, D P Pantaleone, P P Taylor, I G Fotheringham, D J Ager and N J Turner (2002) *Tetrahedron Lett.* 43, 707-710.
(15) P L Dostert, M S Benedetti and K F Tipton (1989) *Medicinal Research Reviews* 9, 45-89.
(16) J D Sutherland (2000) *Curr. Opinion. Chem. Biol.* 263.
(17) F H Arnold (1998) *Acc. Chem. Res.* 31, 125.

The invention claimed is:

1. A method for the enantiomeric conversion of amines comprising treating a chiral amine of Formula I or a mixture of amine enantiomers of Formula I

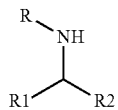

in which:
a) R is H or C1-4alkyl; R1 and R2 are independently selected from substituted or unsubstituted C1-10alkyl, C1-10 alkenyl, C1-10cycloalkyl, C1-10heterocycle, C1-10aryl, C1-10heteroaryl, C1-4-alkyl-aryl, C1-4alkyl-heteroaryl, C1-4-alkyl-C1-6cycloalkyl and C1-4-alkyl-C1-6heterocycle; or
b) R is H or C1-4alkyl, R1 and R2 together form a substituted or unsubstituted C1-10cycloalkyl ring system or C1-10aryl ring containing one or more heteroatoms; or
c) R1 and R1 together form a substituted or unsubstituted C1-10 cycloakyl or C1-10aryl ring system which may contain one or more heteroatoms and R2 is defined as in a) above;
with a Type II amine oxidase enzyme capable of catalyzing oxidation of the amine in a stereoselective manner and treating with a reducing agent wherein said Type II amine oxidase enzyme is selected from the group consisting of:
a Type II amine oxidase enzyme which has a sequence differing from wild-type *Aspergillus niger* monoamine oxidase by mutation in the region of amino acids 334-350 of SEQ ID NO:1;
a Type II amine oxidase enzyme having a sequence differing from wild type *A. niger* monoamine oxidase by mutation of the amino acid at position number 336 of SEQ ID NO:1;
a Type II amine oxidase enzyme having the amino acid sequence of SEQ ID NO:2; and
a Type II amine oxidase enzyme which is a variant of *A. niger* monoamine oxidase of SEQ ID NO:1, said variant having asparagine replaced by serine at amino acid position number 336 of SEQ ID NO:1, and one or more of the following:
(a) methionine replaced by lysine at amino acid position number 348 of SEQ ID NO:1,
(b) arginine replaced by leucine at amino acid position number 259 of SEQ ID NO:1, or
(c) arginine replaced by leucine at amino acid position number 260 of SEQ ID NO:1.

2. The method according to claim 1 in which the Type II amine oxidase enzyme has a sequence differing from wild-type *Aspergillus niger* monoamine oxidase by mutation in the region of amino acids 334-350 of SEQ ID NO:1.

3. The method according to claim 1 in which the Type II amine oxidase enzyme has a sequence differing from wild type *A. niger* monoamine oxidase by mutation of the amino acid at position number 336 of SEQ ID NO:1.

4. The method according to claim 1 in which has the amino acid sequence of SEQ ID NO:2.

5. The method according to claim 1 in which the Type II amine oxidase enzyme is a variant of *A. niger* monoamine oxidase of SEQ ID NO:1, said variant having asparagine replaced by serine at amino acid position number 336 of SEQ ID NO:1, and methionine replaced by lysine at amino acid position number 348 of SEQ ID NO:1.

6. The method according to claim 1 in which the Type II amine oxidase enzyme is a variant of *A. niger* monoamine oxidase of SEQ ID NO:1, said variant having asparagine replaced by serine at amino acid position number 336 of SEQ ID NO:1, and one or more of the following:
 (a) methionine replaced by lysine at amino acid position number 348 of SEQ ID NO:1,
 (b) arginine replaced by leucine at amino acid position number 259 of SEQ ID NO:1, or
 (c) arginine replaced by leucine at amino acid position number 260 of SEQ ID NO:1.

* * * * *